United States Patent [19]

Lawes et al.

[11] Patent Number: 5,176,681

[45] Date of Patent: Jan. 5, 1993

[54] INTRAMEDULLARY INTERTROCHANTERIC FRACTURE FIXATION APPLIANCE AND FITTING DEVICE

[75] Inventors: Peter Lawes, Maidenhead; Stephen Taylor, Basildon; Philip J. Adcock, Great Wakering, all of England

[73] Assignee: Howmedica International Inc., Clare, Ireland

[21] Appl. No.: 281,730

[22] Filed: Dec. 9, 1988

[30] Foreign Application Priority Data

Dec. 14, 1987 [GB] United Kingdom ............ 8729146
Jun. 23, 1988 [GB] United Kingdom ............ 8814920

[51] Int. Cl.⁵ ............................................. A61B 17/58
[52] U.S. Cl. ........................................ 606/64; 606/65; 606/98
[58] Field of Search ........... 128/92 Y, 92 YZ, 92 YY, 128/92 YK, 92 YW, 92 YV, 92 YS, 92 YJ, 92 YF, 92 VD, 92 YP, 92 YE, 92 V, 92 VY, 92 W, 92 VT; 606/64, 65, 98

[56] References Cited

U.S. PATENT DOCUMENTS

| | | | |
|---|---|---|---|
| 2,562,419 | 7/1951 | Ferris | 128/92 V |
| 3,433,220 | 3/1969 | Zickel | 128/92 YY |
| 4,095,591 | 6/1978 | Graham, Jr. et al. | 128/92 YV |
| 4,103,683 | 8/1978 | Neufeld | 128/92 YZ X |
| 4,465,065 | 8/1984 | Gotfried | 128/92 YV X |
| 4,622,959 | 11/1986 | Marcus | 128/92 YZ |
| 4,628,923 | 12/1986 | Medoff | 128/92 YV |
| 4,653,487 | 3/1987 | Maale | 129/92 YZ X |
| 4,697,585 | 10/1987 | Williams | 128/92 YY X |
| 4,705,027 | 11/1987 | Klaue | 128/92 VD X |
| 4,733,654 | 3/1988 | Marino | 128/92 YY |
| 4,776,330 | 10/1988 | Chapman et al. | 128/92 YY |

FOREIGN PATENT DOCUMENTS

| | | |
|---|---|---|
| 0187283 | 7/1986 | European Pat. Off. |
| 0257118 | 3/1988 | European Pat. Off. |
| 8528770 | 12/1985 | Fed. Rep. of Germany |
| 8620399 | 11/1986 | Fed. Rep. of Germany |
| 515914 | 3/1955 | Italy ............................ 128/92 VD |

OTHER PUBLICATIONS

Journal De Chirurgie, vol. 42, Issue No. 3 pp. 375-376, Sep. 1933.
Wisconsin Medical Journal; A Fluoroscopic Technique For Nailing Fractures May 1939.
Siebrandt Manf. Co. Advertisement Jul. 1939.
Acme Engineering Co. Advertisement Jul. 1949.

Primary Examiner—Robert A. Hafer
Assistant Examiner—Kevin G. Rooney
Attorney, Agent, or Firm—Diller, Ramik & Wight

[57] ABSTRACT

An intramedullary intertrochanteric fracture fixation appliance comprising an intramedullary rod having an angulated opening to receive a femoral neck screw, said rod having a co-axial bore extending into said angulated opening, anti-rotation means located in said bore to selectively prevent rotation of said neck screw in the rod and the open end of said bore being provided with means to positively locate a removable fitting device on the proximal end of the rod and so that said anti-rotation means can be operated with the fitting device in position.

34 Claims, 3 Drawing Sheets

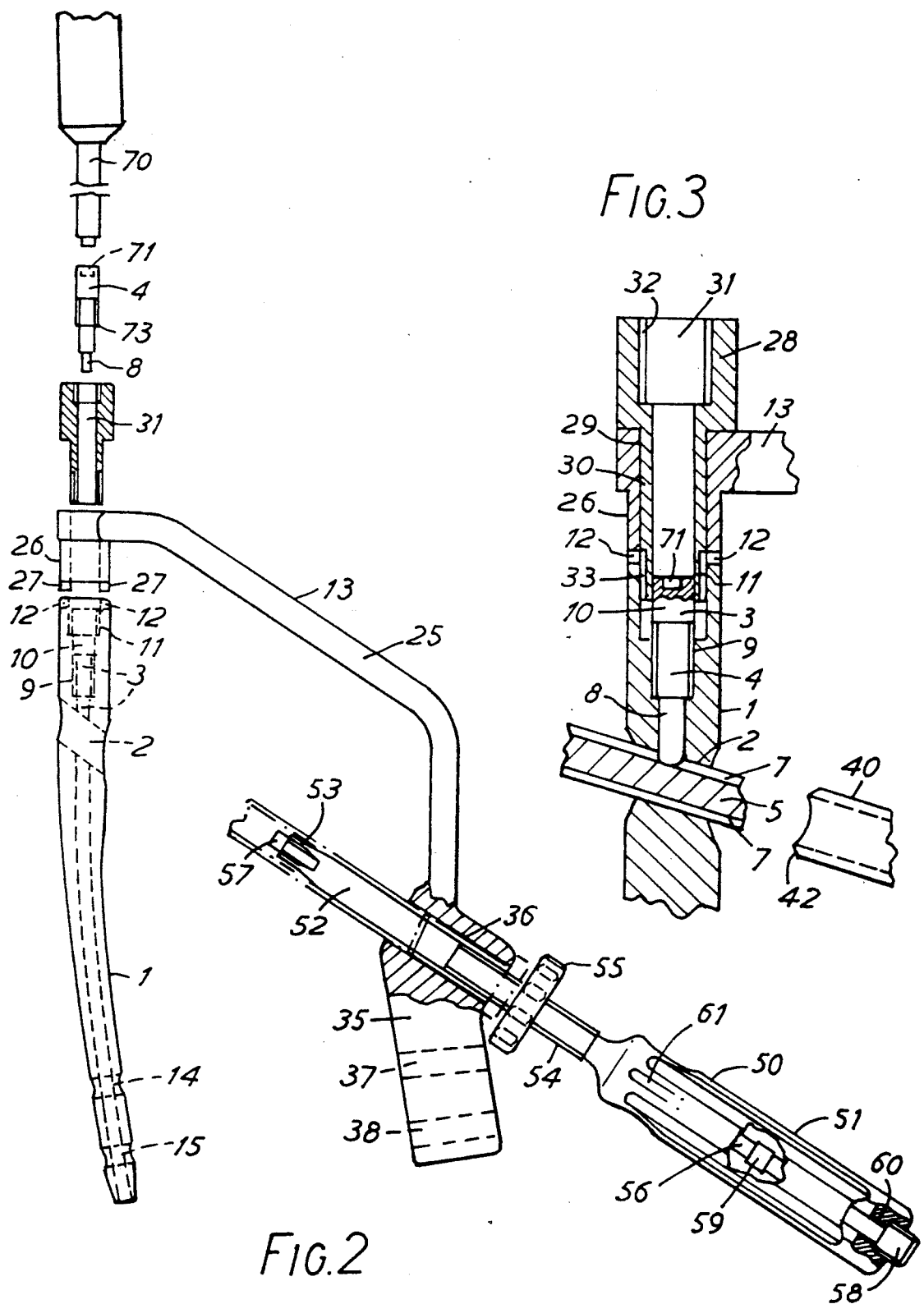

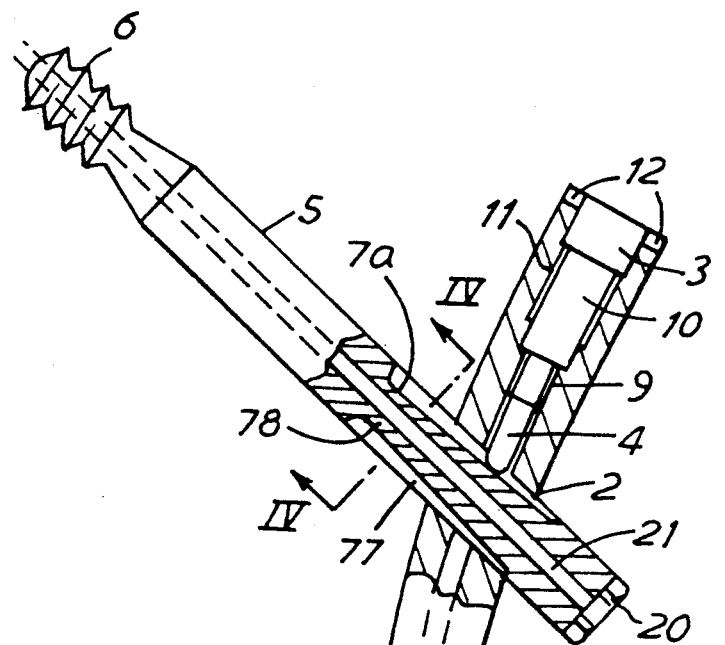
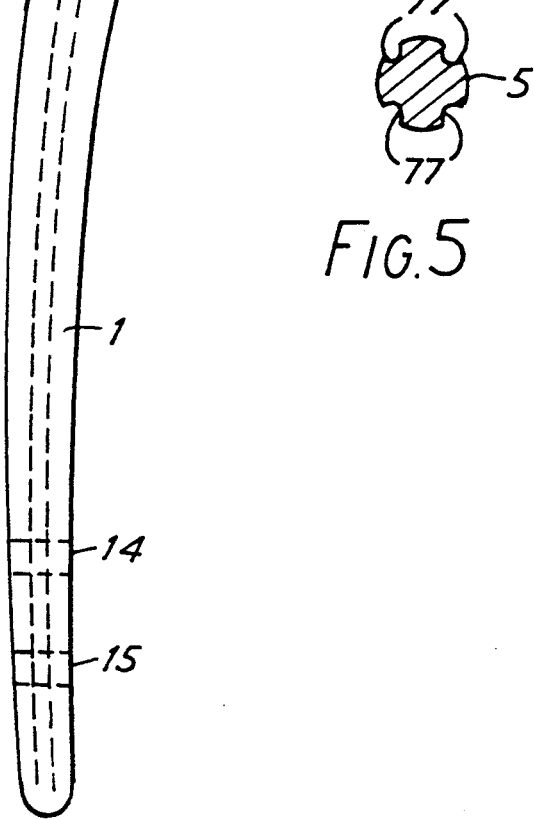
Fig.4
Fig.5

INTRAMEDULLARY INTERTROCHANTERIC FRACTURE FIXATION APPLIANCE AND FITTING DEVICE

BACKGROUND OF THE INVENTION

This invention relates to an intramedullary intertrochanteric fracture fixation appliance and a removable fitting device for use therewith.

Intramedullary intertrochanteric fracture fixation devices are known which comprise an intramedullary rod having an angulated opening to receive a femoral neck screw which is sometimes provided in the form of a lag screw. The intramedullary rod is fitted in the intramedullary canal of the femur and the neck screw passes through an opening in the intramedullary rod, through the neck of the femur and into the head. With this kind of device it is possible to produce tension in the neck screw to pull the head and neck of the femur together and means can be provided to prevent the screw rotating both during this operation and in its final position. This can be provided by the provision of grooves in the neck screw into which a set screw can be located thus allowing the neck screw to slide but not rotate and when the procedure has been completed the set screw can be tightened up to hold the parts in a fixed position. Alternatively, some surgeons prefer to leave the set screw loose merely preventing rotation as required for the particular patient.

It is also known to provide a fitting device to assist in locating the various parts during the operation. Thus, the fitting device may be arranged to clamp to the upper end of the intramedullary rod and to provide a guide to enable a hole to be bored in the head of the femur to accept the neck screw. The guide can also remain in position to assist in guiding the compression screw it is being screwed into position. Such fitting while devices can also provide guides for drilling holes further down the femur to allow location screws to be passed through the lower end of the intramedullary rod to locate the intramedullary rod.

A disadvantage with the arrangement set forth above is that the fitting device has to be removed to allow the set screw, or other means to hold the neck screw in position, to be operated and there is a tendency for the neck screw to unthread or move longitudinally in the intramedullary rod while the fitting device is being removed and before the set screw can be inserted, and an object of the present invention is to provide such an intramedullary intertrochanteric fracture fixation appliance which has provision for carrying out the operation of locking the neck screw and avoiding its becoming loosened or moving during the operation.

SUMMARY OF THE INVENTION

According to the present invention an intramedullary intertrochanteric fracture fixation appliance comprises an intramedullary rod having an angulated opening to receive a femoral neck screw, said rod having a co-axial bore extending into said angulated opening, anti-rotation means located in said bore to selectively prevent rotation of said neck screw in the rod and the open end of said bore being provided with means to positively locate a removable fitting device on the proximal end of the rod such that said anti-rotation means can be operated with the fitting device in position.

Thus, any operation of the anti-rotation means can take place with the fitting device still in position and the risk of the neck screw loosening is reduced.

There are also other advantages in as much that a guide means for guiding means for drilling the hole in the head and neck of the femur can also be left in position while the anti-rotation means are fitted.

A further advantage is that the complete operation can be carried out and completed before removal of the fitting appliance said that the operative steps are not divided up.

Preferably the anti-rotation means can also act to lock the neck screw in position in the rod.

Thus, the neck screw can be provided with longitudinally extending grooves which can be engaged by a set screw located in said bore to selectively prevent rotation of the neck screw or clamp it in position.

The proximal end of the neck screw can be provided with means to receive the removable fitting device.

The invention also includes an intramedullary intertrochanteric fracture fixation appliance as set forth in combination with a removable fitting device provided with means for positive location in the bore on the proximal end of the rod, means allowing location of the set screw, and guide means for accurately guiding means for forming a hole in the femur end head to receive said femoral neck screw.

Preferably the guide means include a tunnel locator.

One end of the tunnel locator can be adapted to engage and locate on the intramedullary rod.

The fixing device may also include a removable tension adjuster which extends through the tunnel locator for connection to the proximal end of the neck screw and has adjustment means for applying a tension to said screw.

The adjustment means can be arranged to engage the proximal end of the tunnel locator to apply a compression thereon between said adjustment means and the intramedullary rod.

Preferably the removable tension adjuster has means to engage driving means on the neck screw to drive it into position by rotation thereof.

The removable tension adjuster can therefore comprise a screw driver with a hollow shaft, the distal end of said shaft having means to engage the neck screw to drive it into position and an operating handle, a tensioning adjuster extending axially through said hollow shaft, one end of said adjuster being screw threaded to engage a threaded bore on the end of the neck screw and the other end having an operating portion by which it can be rotated, the hollow shaft carrying a screw threaded adjuster which can act against the proximal end of the tunnel locator.

The removable fitting device can also be provided with means for guiding means for forming a hole or holes in the femur to receive screws or pins to locate the distal end of the intramedullary rod.

Two sizes of set screw can be provided for use in the intramedullary rod, one screw being of a substantially plain configuration and the other having a flange which can engage abutment means on the intramedullary rod to locate its axial position so that it can enter the grooves in the neck screw but not lock it in position.

It is sometimes advantageous to be able to allow a limited amount of relative sliding movement between the neck screw and an intramedullary rod where weight is applied to the hip and another aspect of the present invention is intended to provide a construction in which such a facility is available.

According to another aspect of the present invention therefore an intramedullary intertrochanteric fracture fixation appliance comprises an intramedullary rod having an angulated opening to receive a femoral neck screw, said rod having a co-axial bore extruding into said angulated opening, anti-rotation means to selectively prevent rotation of said neck screw in the rod and adjustable means to allow relative movement between the rod and the screw over a selected portion of the length thereof.

Preferably the adjustable means may comprise an adjustable stop and the anti-rotation means may also be provided by the same stop.

The anti-rotation means can also act to lock the neck screw in position.

Thus, the invention in this form provides three alternatives for a surgeon. He can allow a limited relative movement between the screw and the rod, locking between the two parts or relative sliding movement over a selected portion of the length of the screw.

In a preferred construction the neck screw is provided with longitudinally extending grooves or flats which can be engaged by a set screw located in said bore to selectively prevent rotation of the neck screw or clamp it in position.

The grooves or flats can be in the form of inclined ramps which can co-operate with the set screw to provide the selected portion of the length of the screw over which there is relative sliding movement between the screw and the rod.

The open end of the bore in the rod can be provided with means to positively locate a fitting device in the manner set forth above.

The invention can be performed in many ways and two embodiments will now be described by way of example and with reference to the accompanying drawings.

BRIEF DESCRIPTION OF THE DRAWINGS

FIG. 2 is a part cross-sectional side elevation of the device and appliance shown in FIG. 1 showing the various parts ready for assembly.

FIG. 3 is an enlarged cross-sectional view of part of the fixation appliance and fitting device shown in Figures 1 and 2.

FIG. 4 is a part sectional cross-sectional side view of an alternative form of fracture fixation appliance.

FIG. 5 is a cross-sectional view of the neck screw taken along the line IV-IV of FIG. 4.

DESCRIPTION OF THE PREFERRED EMBODIMENTS

Figure 1:
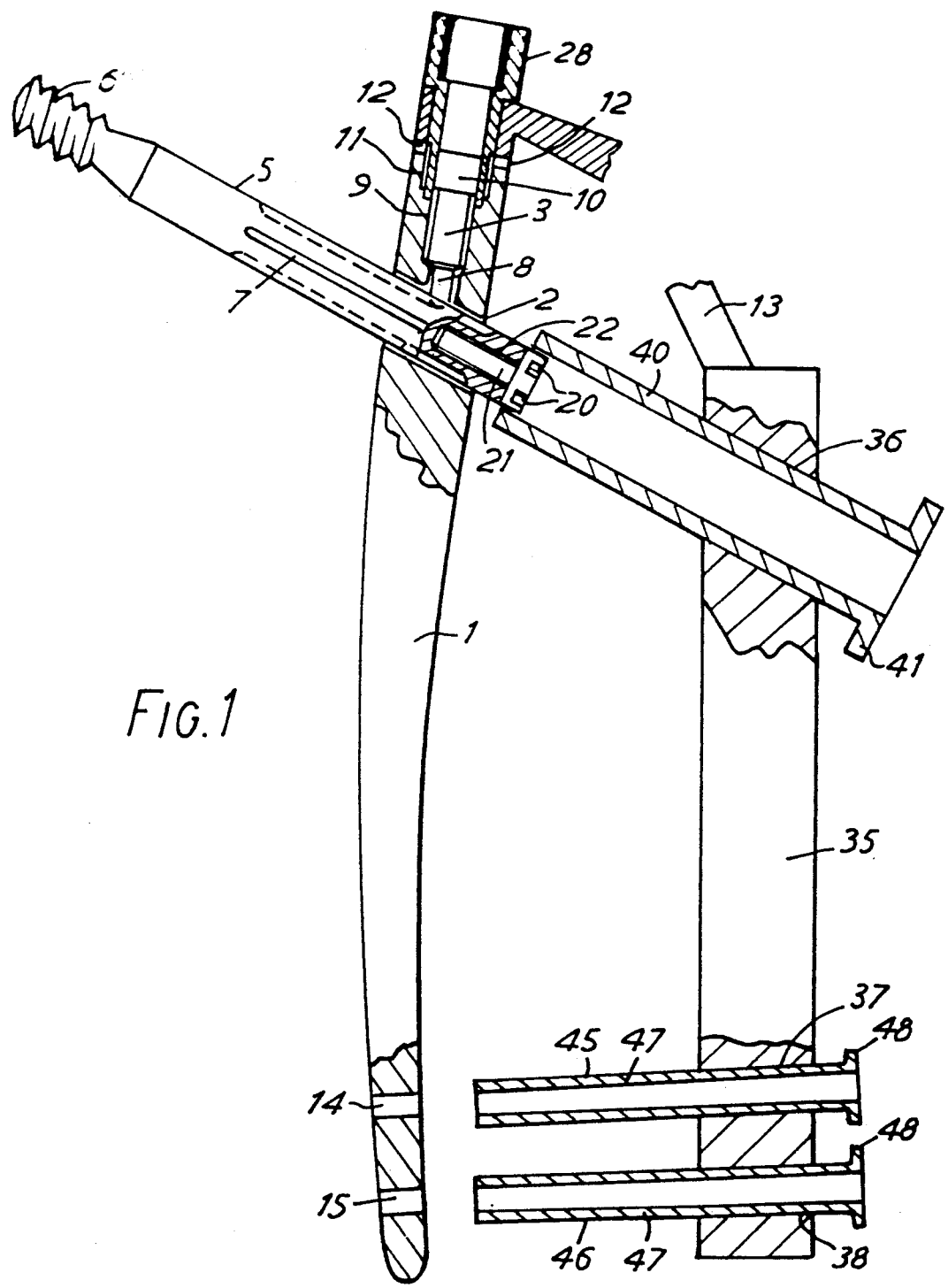
FIG. 1 is a diagrammatic part cross-sectional view of the fracture fixation appliance and fitting device according to the invention.

As shown in FIGS. 1, 2, 3 and 4 of the drawings the intramedullary intertrochanteric fracture fixation appliance comprises an intramedullary rod 1 for introduction into the intramedullary canal of a femur. As is most clearly shown in FIG. 3 the intramedullary rod, has an angulated opening 2 and a co-axial bore 3 which opens into the angulated opening 2 and in which is located anti-rotation means in the form of a set screw 4.

Located in the angulated opening 2 is a femoral neck screw 5 in the form of a lag screw, one end of which carries a coarse screw thread 6 and which is provided with four longitudinally extending grooves 7. The lower end of the set screw 4 is provided with a location boss 8 which is dimensioned so that it can engage one of the grooves 7 and thus prevent rotation of the neck screw 5 when the set screw 4 is in the position shown in FIGS. 1 and 3. In order to receive set screw 4 the bore 3 is screw threaded at 9 and the upper end of the bore 3 indicated by reference numeral 10 (FIG. 4), is of an enlarged diameter and is also screw threaded at 11. The proximal end of the intramedullary rod 1 is provided with two radially extending slots 12 to receive and locate a fitting device indicated by reference numeral 13 FIGS. 1 and 3 and the distal end of the rod 1 is provided with two holes 14 and 15 to receive pins or screws to fix and locate that end of the rod in the bone.

The proximal end of the neck screw 5 is provided with driving means in the form of circumferentially opposed slots 20 and is formed with a bore 21 which is screw threaded at 22 to receive a removable tension adjuster to be described hereunder.

The fitting device 13 comprises an angulated arm 25 one end of which carries a boss 26 the lower end of which is provided with pegs 27, as is most clearly shown in FIG. 2, and which are shaped to engage in the slots 12 in the proximal end of the intramedullary rod 1. A securing bolt 28 (FIG. 3) is provided with a shank 29 which is a close sliding fit in a bore 30 in the boss 26. The securing bolt 28 (FIG. 3) has a stepped bore 31 the upper enlarged end of which is screw threaded at 32. The lower end of the shank 29 also carries an external screw thread 33 which is adapted to engage with the screw thread 11 in the bore 10 of the rod 1 so that the boss 26 can be firmly clamped to the upper end of the intramedullary rod 1 and held against rotation by the pegs 27.

The other end of the angulated arm 25 carries a guide block 35 which is provided with an angulated bore 36 and two further alignment bores 37 and 38. The positioning of the bore 36 is arranged so that when the fitting device is clamped in position on the rod 1 the bore 36 is accurately aligned with the angulated opening or hole 2 in the rod 1. Similarly the bores 37 and 38 are aligned with the holes 14 and 15 in the rod 1.

Also provided are three tunnel locators (FIG. 1). The locator for the angled bore 36 comprises a tubular portion 40 one end of which carries a flange 41 and the other end of which is shaped as shown at 42 (FIG. 3) to engage the circumferential shape of the rod 1 in close alignment and so that it is held against rotation. The other tunnel locators 45 and 46 also consist of tubes 47 with flanged ends 48. As will be seen from FIG. 1 the tunnel locators 40, 45, 46 can be positioned in the respective bores 36, 37 and 38 in the guide block 35 and are removable slide fits therein. The length of the locators 40, 45, 46 is arranged so that they can extend from the guide block 35 up to and in engagement with the intramedullary rod 1.

A removable tension adjuster is provided which can extend through the tunnel locator 40 for connection to the proximal end of the neck screw 5 and adjustment means are provided for applying a tension to the screw when it is in position in the bone in order to enable the fractured portion to be pulled into close proximity with the remainder of the bone. The tension adjuster comprises a hollow screw driver 50 (FIG. 2) which has a hollow handle 51, a hollow shank 52 and a substantially cruciform shaped end 53 which can engage in the slots 20 in the end of the compression screw so that the screw 5 can be turned. The outer circumference of the shank 52 is screw threaded at 54 and carries a hand wheel 55. Extending axially through the screw driver 50 is a tensioning adjuster in the form of a tubular rod 56 one end of which is screw threaded at 57 and the other end of which is provided with a boss 58 by which the rod may be rotated. The rod is free to slide axially within the screw driver 50 and a portion of the rod is provided with an upstanding screw thread 59 which can be screwed through a co-operating screw thread 60 provided in a bore in the distal end of the handle 51. The length of the rod 56 is arranged so that the screw thread 57 can protrude from the end of the shank 52 with the boss 58 located against the end of the handle. Four arrows 61 are marked on the diametrically opposed sides of the handle 51 for reasons to be described hereunder. The shank 52 is an accurate sliding fit in the bore of the tunnel locator 40.

The thread 50 of the rod 56 prevents the rod falling out of the screw driver but when it is desired to remove the rod 56 for sterilization purposes it is merely necessary to withdraw it until the screw thread 59 engages the screw thread 60 and then rotate it until the rod is free.

A further screw driver 70 (FIG. 2) is also provided which has a suitably shaped end to engage a socket 71 provided in the end of the set screw 4.

A location rod (not shown) is also provided in the form of a simple length of circular rod of the same diameter as the neck screw 5, one end of the rod being bent over to form an arm. The use of this rod will be described later.

When the operation is to be carried out the intramedullary rod 1 is located in the intramedullary canal of the femur in the usual way and the fitting device 13 is placed in position by engaging the pegs 27 in the slots 12 and inserting the securing bolt 28, the thread 33 on the bolt 28 engaging the thread 11 in the upper end of the bore 10 in the rod 1 and thus clamping the fitting device against rotation or rocking movement. The tunnel locator 40 is now placed in position in the bore 36 and a hole is bored through the femur, the neck of the femur and into the head thereof to receive the femoral neck screw 5. The tunnel locator 40 therefore acts as a guide. During this part of the operation the fractured neck or head of the femur can be displaced and it is necessary to draw it into engagement with the remainder of the bone. In order to achieve this the set screw 4 is inserted down the bore 31 of the bolt 28 so that its screw thread engages the screw thread 9 in the lower end of the bore 3. The length of rod (not shown) previously referred to is now inserted into the tunnel locator 40 so that it extends into the opening 2 and the set screw 4 is advanced until it touches the rod. The surgeon now knows that the end of the set screw 4 is approximately in- line with the surface of the opening 2. The neck screw 5 is now screwed into position by operating the screw driver 50, its cruciform end 53 engaging the slots 20 in the end of the screw 5, and the arrows 61 on the screwdriver are used to align one of the grooves 7 in the uppermost position. The set screw 4 is now turned downwards with the screwdriver 70 until the lower end 8 of the set screw 4 is engaged within one of the grooves 7. Provided the screw 4 is not tightened the neck screw 5 now has the facility to slide in the opening 2 but is locked against rotation. With the neck screw 5 in this position the inner rod 56 of the screwdriver is now rotated by operating the knob 58 and so that the screw thread 57 at its distal end engages the screw thread 21 in the proximal end of the neck screw 5. With the inner rod 56 now held in position on the screw the hand wheel 55 is rotated so that it engages and acts against the flange 41 of the tunnel locator 40. As the other end of the locator 40 engages against the rod 1 further movement of the hand wheel 55 will cause the whole screwdriver 50 to be drawn outwardly taking with it the neck screw 5. As the neck screw 5 is held against rotation by the set screw 4 it merely slides through the opening 2 and draws the head of the femur into close engagement with the rest of the bone. In certain circumstances it is not necessary to maintain the tension in the neck screw 5 and it can be relaxed, the operation of drawing the bones together having been completed. Alternatively, it may be necessary to hold the bones together under tension and in order to achieve this the set screw 4 is now-tightened down further so that it firmly holds the neck screw 5 in position.

The screw driver 50 can now be removed.

Before or after the previous operations the tunnel locators 45 and 46 can be used to accurately drill through the bone so that pins and/or screws can be inserted through them to locate the distal end of the rod 1.

The tunnel locators 40, 45, 46 can also be used for controlling the position and angulation of guide wires, the drills the taps and, as referred to above, the femoral neck screw 5 or other screws.

Thanks to the construction of the securing bolt 28 it is possible to achieve all the necessary actions without removing the fitting device 13 and thus it is not necessary to remove the tunnel locator 40 before fully and finally fitting the implant. This has various advantages, firstly the femoral neck screw 5 can be fully fitted and locked before moving on to fit the optional distal screws in the holes 14 and 15. There is always a risk that while the two distal locking screws are being fitted or while the tunnel locator 40 is being removed the neck screw 5 can rotate (with or without the femoral head also rotating) and this can prevent the set screw 4 from correctly engaging the neck compression screw groove 7.

There are also advantages in completing the implantation and then removing the instrument rather than dividing up the operative steps.

The operating surgeon is given a number of choices; he can either tightly lock the assembly (so that neither sliding nor rotation of the neck screw 5 can occur), or he can fit the set screw 4 so that it allows sliding and prevents rotation.

As there will be a family of sizes of both intramedullary rods 1 and neck screws 5 it is difficult to standardize the, distance from the upper end of the intramedullary rod to the neck screws 5 and this poses a constraint on the standardization of set screws.

It is impractical to for the surgeon to check the correct position of the locking screw 4 by direct observation (visually or X-ray) or by feeling the top of said screw 4 relative to the top end of the intramedullary rod 1. In order to do this it would inevitably be necessary to produce a family of set screws. Any error made in the operating theatre (wrong choice of screw size) or made by the manufacturer (screw too short, too long) or incorrectly identified, would render the design non-foolproof.

A further feature of the present invention therefore is that it is possible to have one size of set screw 4 only and which is fitted to the intramedullary rod 1 before the femoral neck screw 5 is installed in the manner described above.

To recap this procedure therefore, first a rod corresponding to the diameter of the neck screw 5 is passed through the lateral femoral cortex (after reaming using the tunnel locator 40) and juts through the intramedullary rod 1. The set screw 4 is now driven in until it jams against the rod 1. This position is determined when the rod will no longer freely rotate and it is for this reason that the end of the rod is provided with an arm. The set screw 4 is now backed off approximately one turn to release the rod, the rod is removed, the appropriate femoral neck screw 5 is connected and inserted in the manner described above and with one of the grooves 7 directly beneath the set screw 4. The set screw 4 is now driven in more than one turn (depending on the choice of screw pitch) and it is then definitely engaging in the neck screw groove 7.

As described above, if desired the surgeon can drive the set screw 4 a further turn to cause it to firmly jam in the groove 7 thereby locking the total assembly and preventing sliding.

If desired this type of set screw 4 can have a Nylok pellet in the thread to prevent involuntary rotations when in service.

Although the above method of operation is practical and simple it does have the disadvantage that the surgeon must remember that after jamming the test rod with the set screw 4 that he backed off one turn (say) then after installing the neck screw 5 that he must rotate the set screw 4 in two turns (say) to prevent sliding of the neck screw 5.

As an alternative a shoulder can be provided in the bore inside each size of intramedullary rod 1 at a fixed height above the opening 2. This shoulder engages with a corresponding shoulder on a set screw of the type shown in FIG. 2 where the shoulder is indicated by reference numeral 73. This shoulder is arranged at a suitable distance from the end 8 of the set screw so that when it engages the shoulder in the rod 1 the end of the screw protrudes into the opening 2 and, provided it is in a groove 7, has sufficient effect to prevent rotation of the neck screw 5 but does not act to lock it in position against sliding. Thus, after installing the neck screw 5 the set screw 4 is merely driven down to the shoulder.

The remainder of the steps of the operation will be as set forth above to avoid the risk of a bone chip fouling said screw thread and causing the surgeon to believe mistakenly that the set screw 4 was fully home.

With a set screw 4 of this type however it will be appreciated that there is no provision for totally locking the assembly against sliding although it will lock it against rotation.

To overcome this difficulty a second set screw is provided which does not have a shoulder and which is slightly longer than the first set screw referred to above so that when it is screwed in to its full extent it locks in the groove 7 and not only prevents rotation but also prevents sliding. As the shoulder is not required on this second screw it is possible to design it to be visually different from the first, that is there is no shoulder, thereby reducing the risk of error by the manufacturer, surgeon or nurse in incorrectly identifying the required screw. If desired the screw with a shoulder can be simply labled "sliding" while the slightly longer screw without the shoulder can simply be labled "locking". A screw without a shoulder is shown in FIG. 1 and a screw with a shoulder in FIGS. 2 and 3.

FIGS. 4 and 5 show an alternative construction of fixation appliance but the same reference numerals are used to indicate similar parts to those shown in FIGS. 1, 2 and 3. In this construction the femoral neck screw 5 in the form of a lag screw is provided with four longitudinally extending ramp shaped grooves 77. As will be seen from the drawing, the shallow ends 78 of the ramps, that is the deeper ends of the grooves 77 are towards the threaded end 6 of the neck screw 5.

As will be seen the set screw 4 now acts not only as anti-rotation means but as an adjustable stop for limiting the length of sliding movement of the neck screw 5 in relation to the rod 1. Thus, movement toward the left hand side of the drawing, that is in the direction of the screw threaded portion of the rod 1, by the screw 5 is restricted by the set screw 4 engaging the rising ramp in the slot 77 but, because the slot is angled away from the set screw 4 in the other direction, there is relative sliding movement between the parts in that direction.

The surgeon now has three choices, when the fractured femur has been drawn together. The surgeon can screw down the set screw 4 to cause it to firmly jam in the groove 77 thereby locking the total assembly and preventing sliding. Alternatively, the surgeon may merely allow the screw 4 to lightly engage in the groove 77 thus allowing relative sliding movement between the parts but preventing turning. The third alternative is to screw the set screw 4 down until it engages the ramp 77, for example in the manner as shown in FIG. 4 of the drawings. In this position relative movement between the parts is allowed when compression is applied to the bone fracture. This compression is therefore maintained when the fitting device 13 referred to above is removed. The neck screw 5 is still free to move when body weight or muscle activity takes effect on the hip joint but the set screw 4 limits the relative movement over a selected portion of the length of the neck screw 5.

We claim

1. An intramedullary intertrochanteric fracture fixation appliance comprising an intramedullary rod having proximal and distal ends, an angulated opening in said proximal end, said rod having a generally axial bore through said proximal end opening into said angulated opening, a femoral neck screw at least partially housed in and projecting from said angulated opening, said neck screw having proximal and distal ends, anti-rotation means operative through said bore for selectively preventing rotation of said neck screw in said rod opening, said rod proximal end having means for positively locating a removable fitting device in position on said rod proximal end, and said positive locating means being constructed and arranged for said anti-rotation means to be operated with the fitting device in its positively located position.

2. The appliance as defined in claim 1 wherein said anti-rotation means is constructed and arranged for locking the neck screw in position in the rod opening.

3. The appliance as defined in claim 1 wherein said anti-rotation means includes at least one longitudinally extending groove in said neck screw which can be engaged by a set screw located in said bore.

4. The appliance as defined in claim 1 wherein said neck screw proximal end includes means for receiving a removable fitting device.

5. The appliance as defined in claim 1 including a removable fitting device positively located on the rod proximal end by said locating means, said removable fitting device having an access opening means through which said anti-rotation means can be operated when the fitting device is in its positively located position, and said removable fitting device having guide means for accurately guiding a hole forming mechanism adapted to form a hole in a femoral end head into which said neck screw is adapted to be received.

6. The appliance as defined in claim 1 including a removable fitting device positively located on the rod proximal end by said locating means, said removable fitting device having an access opening means through which said anti-rotation means can be operated when the fitting device is in its positively located position, and said removable fitting device having guide means for accurately guiding a hole forming mechanism adapted to form a hole in a femoral end head into which said neck screw is adapted to be received, and said guiding means includes a tunnel locator.

7. The appliance as defined in claim 1 including a removable fitting device positively located on the rod proximal end by said locating means, said removable fitting device having an access opening means through which said anti-rotation means can be operated when the fitting device is in its positively located position, and said removable fitting device having guide means for accurately guiding a hole forming mechanism adapted to form a hole in a femoral end head into which said neck screw is adapted to be received, said guiding means includes a tunnel locator, and said tunnel locator is aligned with said angulated opening.

8. The appliance as defined in claim 1 including a removable fitting device positively located on the rod proximal end by said locating means, said removable fitting device having an access opening means through which said anti-rotation means can be operated when the fitting device is in its positively located position, and said removable fitting device having guide means for accurately guiding a hole forming mechanism adapted to form a hole in a femoral end head into which said neck screw is adapted to be received, said guiding means includes a tunnel locator, said tunnel locator is aligned with said angulated opening, a removable tension adjustor extending through said tunnel locator adapted for connection to the neck screw proximal end, and said tension adjuster includes adjustment means for applying tension to said neck screw.

9. The appliance as defined in claim 1 including a removable fitting device positively located on the rod proximal end by said locating means, said removable fitting device having an access opening means through which said anti-rotation means can be operated when the fitting device is in its positively located position, and said removable fitting device having guide means for accurately guiding a hole forming mechanism adapted to form a hole in a femoral end head into which said neck screw is adapted to be received, said guiding means includes a tunnel locator, said tunnel locator is aligned with said angulated opening, a removable tension adjuster extending through said tunnel locator adapted for connection to the neck screw proximal end, said tension adjuster includes adjustment means for applying tension to said neck screw, said tunnel locator includes proximal and distal ends, and said adjustment means engages the tunnel locator proximal end to apply a compression force thereon between said adjustment means and said rod.

10. The appliance as defined in claim 1 including a removable fitting device positively located on the rod proximal end by said locating means, said removable fitting device having an access opening means through which said anti-rotation means can be operated when the fitting device is in its positively located position, and said removable fitting device having guide means for accurately guiding a hole forming mechanism adapted to form a hole in a femoral end head into which said neck screw is adapted to be received, said guiding means includes a tunnel locator, said tunnel locator is aligned with said angulated opening, a removable tension adjuster extending through said tunnel locator adapted for connection to the neck screw proximal end, said tension adjuster includes adjustment means for applying tension to said neck screw, said tunnel locator includes proximal and distal ends, said adjustment means engages the tunnel locator proximal end to apply a compression force thereon between said adjustment means and said rod, and said tension adjuster includes means to drivingly engage said neck screw to rotate the same to a desired position of fixation.

11. The appliance as defined in claim 1 including a removable fitting device positively located on the rod proximal end by said locating means, said removable fitting device having an access opening means through which said anti-rotation means can be operated when the fitting device is in its positively located position, and said removable fitting device having guide means for accurately guiding a hole forming mechanism adapted to form a hole in a femoral end head into which said neck screw is adapted to be received, said guiding means includes a tunnel locator, said tunnel locator is aligned with said angulated opening, a removable tension adjuster extending through said tunnel locator adapted for connection to the neck screw proximal end, said tension adjuster includes adjustment means for applying tension to said neck screw, said tunnel locator includes proximal and distal ends, and said adjustment means engages the tunnel locator proximal end to apply a compression force thereon between said adjustment means and said rod, said tension adjuster includes means to drivingly engage said neck screw to rotate the same to a desired position of fixation, said tension adjuster includes a screwdriver having a hollow shaft, said hollow shaft having proximal and distal ends, said shaft distal end having means for engaging said neck screw rotated to is position of fixation, said shaft having an operating handle, said tensioning adjuster further including a tension adjusting mechanism extending axially through said hollow shaft, said tensioning adjusting mechanism having proximal and distal ends, said tension adjusting mechanism distal end being threaded to engage threads of said neck screw proximal end, and said tension adjusting mechanism proximal end having means for rotating said tension adjusting mechanism.

12. The appliance as defined in claim 1 including a removable fitting device positively located on the rod proximal end by said locating means, said removable fitting device having an access opening means through which said anti-rotation means can be operated when the fitting device is in its positively located position, said removable fitting device having guide means for accurately guiding a hole forming mechanism adapted to form a hole in a femoral end head into which said neck screw is adapted to be received, and said removal fitting device further includes means for accurately guiding a hole forming mechanism adapted to form a hole in the femur for rod distal end securement.

13. The appliance as defined in claim 1 wherein said anti-rotation means includes at least one longitudinally extending groove in said neck screw which can be engaged by a set screw located in said bore, and said set screw further locks against said neck screw to prevent rotation thereof.

14. An intramedullary intertrochanteric fracture fixation appliance comprising an intramedullary rod having proximal and distal ends, an angulated opening in said proximal end, said rod having a generally axial bore through said proximal end opening into said angulated opening, a femoral neck screw at least partially housed in and projecting from said angulated opening, anti-rotation means including locking means operative through said bore for selectively preventing rotation of said neck screw in said rod opening, and adjustable means for permitting sliding movement between said rod and said neck screw along a portion of the length of said neck screw in only one direction to maintain bone fragments on opposite sides of a fracture under compression while said anti-rotation means remains operative to prevent rotation of said neck screw.

15. The appliance as defined in claim 14, wherein said adjustable means includes an adjustable stop.

16. The appliance as defined in claim 14, wherein said anti-rotation means includes an adjustable stop.

17. The appliance as defined in claim 14, wherein said adjustable means and said anti-rotation means include an adjustable stop.

18. The appliance as defined in claim 14, wherein said anti-rotation means is also constructed and arranged for locking said neck screw against sliding movement.

19. The appliance as defined in claim 14, wherein said anti-rotation means includes a longitudinally extending groove formed in said neck screw and a set screw located in said bore having a distal end received in said groove.

20. The appliance as defined in claim 14, wherein said locking means is a set screw.

21. The appliance as defined in claim 14, wherein said adjustable means is operable for maintaining a fracture under compression only when said anti-rotation means prevents rotation of said neck screw in said rod opening.

22. The appliance as defined in claim 14, wherein said locking means is operative in (a) one position in which neck screw rotation is prevented but neck screw axial movement is permitted in opposite direction and (b) another position in which neck screw rotation is prevented but neck screw axial movement is permitted in only one direction.

23. An intramedullary intertrochanteric fracture fixation appliance comprising an intramedullary rod having proximal and distal ends, an angulated opening in said proximal end, said rod having a generally axial bore through said proximal end opening into said angulated opening, a femoral neck screw at least partially housed in and projecting from said angulated opening, anti-rotation means operative through said bore for selectively preventing rotation means operative through said bore for selectively preventing rotation of said neck screw in said rod opening, adjustable means for effecting sliding movement between said rod and said neck screw over a selected portion of the length of said neck screw while sand anti-rotation means remains operative to prevent rotation of said neck screw, said anti-rotation means includes a longitudinally extending groove formed in said neck screw and a set screw located in said bore having a distal end received in said groove, and wherein said groove is in the form of an inclined ramp which cooperates with said set screw to provide the selected length of sliding movement along said neck screw.

24. An intramedullary intertrochanteric fracture fixation appliance comprising an intramedullary rod having proximal and distal ends, an angulated opening in said proximal end, said rod having a generally axial bore through said proximal end opening into said angulated opening, a femoral neck screw at least partially housed in and projecting from said angulated opening, anti-rotation means operative through said bore for selectively preventing rotation of of said neck screw in said rod opening, adjustable means for effecting sliding movement between said rod and said neck screw over a selected portion of the length of said neck screw while sand anti-rotation means remains operative to prevent rotation of said neck screw, a removable fitting device, said rod proximal end having means for positively locating said removable fitting device in position on said rod proximal end, and said positive locating means being constructed and arranged for said anti-rotation means to be operated with the fitting device in its positively located position.

25. An intramedullary intertrochanteric fracture fixation appliance comprising an intramedullary rod having proximal and distal ends, an angulated opening in said proximal end, said rod having a generally axial bore through said proximal end opening into said angulated opening, a femoral neck screw at least partially housed in and projecting from said angulated opening, anti-rotation means operative through said bore for selectively preventing rotation means operative through said bore for selectively preventing rotation of said neck screw in said rod opening, adjustable means for effecting sliding movement between said rod and said neck screw over a selected portion of the length of said neck screw while sand anti-rotation means remains operative to prevent rotation of said neck screw, a removable fitting device positively located on the rod proximal end by said locating means, said removable fitting device having an access opening means through which said anti-rotation means can be operated when the fitting device is in its positively located position, and said removable fitting device having guide means for accurately guiding a hole forming mechanism adapted to form a hole in a femoral end head into which said neck screw is adapted to be received.

26. An intramedullary intertrochanteric fracture fixation appliance comprising an intramedullary rod having proximal and distal ends, an angulated opening in said proximal end, said rod having a generally axial bore through said proximal end opening into said angulated opening, a femoral neck screw at least partially housed in and projecting from said angulated opening, anti-rotation means operative through said bore for selectively preventing rotation means operative through said bore for selectively preventing rotation of said neck screw in said rod opening, adjustable means for effecting sliding movement between said rod and said neck screw over a selected portion of the length of said neck screw while sand anti-rotation means remains operative to prevent rotation of said neck screw, a removable fitting device positively located on the rod proximal end by said locating means, said removing fitting device having an access opening means through which said anti-rotation means can be operated when the fitting device is in its positively located position, said removable fitting device having guide means for accurately guiding a hole forming mechanism adapted to form a hole in a femoral end head into which said neck screw is adapted to be received, and said guiding means includes a tunnel locator.

27. An intramedullary intertrochanteric fracture fixation appliance comprising an intramedullary rod having proximal and distal ends, an angulated opening in said proximal end, said rod having a generally axial bore through said proximal end opening into said angulated opening, a femoral neck screw at least partially housed in and projecting from said angulated opening, anti-rotation means operative through said bore for selectively preventing rotation means operative through said bore for selectively preventing rotation of said neck screw in said rod opening, adjustable means for effecting sliding movement between said rod and said neck screw over a selected portion of the length of said neck screw while sand anti-rotation means remains operative to prevent rotation of said neck screw, a removable fitting device positively located on the rod proximal end by said locating means, said removing fitting device having an access opening means through which said anti-rotation means can be operated when the fitting device is in its positively located position, said removable fitting device having guide means for accurately guiding a hole forming mechanism adapted to form a hole in a femoral end head into which said neck screw is adapted to be received, and said guiding means includes a tunnel locator, and said tunnel locator is aligned with said angulated opening.

28. An intramedullary intertrochanteric fracture fixation appliance comprising an intramedullary rod having proximal and distal ends, an angulated opening in said proximal end, said rod having a generally axial bore through said proximal end opening into said angulated opening, a femoral neck screw at least partially housed in and projecting from said angulated opening, anti-rotation means operative through said bore for selectively preventing rotation means operative through said bore for selectively preventing rotation of said neck screw in said rod opening, adjustable means for effecting sliding movement between said rod and said neck screw over a selected portion of the length of said neck screw while sand anti-rotation means remains operative to prevent rotation of said neck screw, a removable fitting device positively located on the rod proximal end by said locating means, said removing fitting device having an access opening means through which said anti-rotation means can be operated when the fitting device is in its positively located position, said removable fitting device having guide means for accurately guiding a hole forming mechanism adapted to form a hole in a femoral end head into which said neck screw is adapted to be received, and said guiding means includes a tunnel locator, said tunnel locator is aligned with said angulated opening, a removable tension adjuster extending through said tunnel locator adapted for connection to the neck screw proximal end, and said tension adjuster includes adjustment means for applying tension to said neck screw.

29. An intramedullary intertrochanteric fracture fixation appliance comprising an intramedullary rod having proximal and distal ends, an angulated opening in said proximal end, said rod having a generally axial bore through said proximal end opening into said angulated opening, a femoral neck screw at least partially housed in and projecting from said angulated opening, anti-rotation means operative through said bore for selectively preventing rotation means operative through said bore for selectively preventing rotation of said neck screw in said rod opening, adjustable means for effecting sliding movement between said rod and said neck screw over a selected portion of the length of said neck screw while sand anti-rotation means remains operative to prevent rotation of said neck screw, a removable fitting device positively located on the rod proximal end by said locating means, said removing fitting device having an access opening means through which said anti-rotation means can be operated when the fitting device is in its positively located position, said removable fitting device having guide means for accurately guiding a hole forming mechanism adapted to form a hole in a femoral end head into which said neck screw is adapted to be received, and said guiding means includes a tunnel locator, said tunnel locator is aligned with said angulated opening, a removable tension adjuster extending through said tunnel locator adapted for connection to the neck screw proximal end, and said tension adjuster includes adjustment means for applying tension to said neck screw, said tunnel locator includes proximal and distal ends, and said adjustment means engages the tunnel locator proximal end to apply a compression force thereon between said adjustment means and said rod.

30. An intramedullary intertrochanteric fracture fixation appliance comprising an intramedullary rod having proximal and distal ends, an angulated opening in said proximal end, said rod having a generally axial bore through said proximal end opening into said angulated opening, a femoral neck screw at least partially housed in and projecting from said angulated opening, anti-rotation means operative through said bore for selectively preventing rotation means operative through said bore for selectively preventing rotation of said neck screw in said rod opening, adjustable means for effecting sliding movement between said rod and said neck screw over a selected portion of the length of said neck screw while sand anti-rotation means remains operative to prevent rotation of said neck screw, a removable fitting device positively located on the rod proximal end by said locating means, said removing fitting device having an access opening means through which said anti-rotation means can be operated when the fitting device is in its positively located position, said removable fitting device having guide means for accurately guiding a hole forming mechanism adapted to form a hole in a femoral end head into which said neck screw is adapted to be received, and said guiding means includes a tunnel locator, said tunnel locator is aligned with said angulated opening, a removable tension adjuster extending through said tunnel locator adapted for connection to the neck screw proximal end, and said tension adjuster includes adjustment means for applying tension to said neck screw, said tunnel locator includes proximal and distal ends, and said adjustment means engages the tunnel locator proximal end to apply a compression force thereon between said adjustment means and said rod, and said tension adjuster includes means to drivingly engage said neck screw to rotate the same to desired position of fixation.

31. The appliance as defined in claim 14 including a removable fitting device positively located on the rod proximal end by said locating means, said removable fitting device having an access opening means through which said anti-rotation means can be operated when the fitting device is in its positively located position, said removable fitting device having guide means for accurately guiding a hole forming mechanism adapted to form a hole in a femoral end head into which said neck screw is adapted to be received, said guiding means includes a tunnel locator, said tunnel locator is aligned with said angulated opening, a removable tension adjuster extending through said tunnel locator adapted for connection to the neck screw proximal end, said tension adjuster includes adjustment means for applying tension to said neck screw, said tunnel locator includes proximal and distal ends, said adjustment means engages the tunnel locator proximal end to apply a compression force thereon between said adjustment means and said rod, said tension adjuster includes means to drivingly engage said neck screw to rotate the same to a desired position of fixation, said tension adjustor includes a screwdriver having a hollow shaft, said hollow shaft having proximal and distal ends, said shaft distal end having means for engaging said neck screw rotated to its position of fixation, said shaft having an operating handle, said tensioning adjuster further including a tension adjusting mechanism extending axially through said hollow shaft, said tensioning adjusting mechanism having proximal and distal ends, said tension adjusting mechanism distal end being threaded to engage threads of said neck screw proximal end, and said tension adjusting mechanism proximal end having means for rotating said tension adjusting mechanism.

32. An intramedullary intertrochanteric fracture fixation appliance as claimed in claim 14, in combination with a removable fitting device provided with means for positive location in the bore on the proximal end of the rod, means allowing location of the set screw, guide means for accurately guiding means for forming a hole in the femoral end head to receive said femoral neck screw, and said removal fitting device further including means for guiding a hole forming mechanism adapted to form a hole in the femur for rod distal end securement.

33. An intramedullary intertrochanteric fracture fixation appliance comprising an intramedullary rod having proximal and distal ends, an angulated opening in said proximal end, said rod having a generally axial bore through said proximal end opening into said angulated opening, a femoral neck screw at least partially housed in and projecting from said angulated opening, anti-rotation means operative through said bore for selectively preventing rotation means operative through said bore for selectively preventing rotation of said neck screw in said rod opening, and said anti-rotation means being further cooperative with adjustments means for permitting sliding movement between said rod and said neck screw in only one direction over a selected portion of the length of said neck screw while said anti-rotation means remains operative to prevent rotation of said neck screw.

34. The appliance as defined in claim 33 wherein said anti-rotation means includes a plurality of longitudinally extending grooves formed in said neck screw and a set screw located in said bore having a distal end received in said groove, and each of said grooves in longitudinally tapered for effecting sliding movement in said only one direction.

* * * * *